(12) United States Patent
Koseoglu et al.

(10) Patent No.: US 6,797,172 B2
(45) Date of Patent: Sep. 28, 2004

(54) DEGUMMING OF EDIBLE OILS BY ULTRAFILTRATION

(75) Inventors: Semih Sefa Koseoglu, College Station, TX (US); Walter E. Farr, Memphis, TN (US); Wim F. S. De Greyt, Sinaai (BE); Marc Kellens, Muizen (BE)

(73) Assignee: The Texas A&M University System, College Station, TX (US)

( * ) Notice: Subject to any disclaimer, the term of this patent is extended or adjusted under 35 U.S.C. 154(b) by 122 days.

(21) Appl. No.: 10/296,951

(22) PCT Filed: May 24, 2001

(86) PCT No.: PCT/US01/16747

§ 371 (c)(1),
(2), (4) Date: Nov. 25, 2002

(87) PCT Pub. No.: WO01/89674

PCT Pub. Date: Nov. 29, 2001

(65) Prior Publication Data

US 2003/0209493 A1 Nov. 13, 2003

Related U.S. Application Data

(60) Provisional application No. 60/206,885, filed on May 24, 2000.

(51) Int. Cl.⁷ .............................................. B01D 15/08
(52) U.S. Cl. ..................... 210/651; 210/653; 210/654; 426/490; 426/492; 426/495; 554/175
(58) Field of Search ................................ 210/180, 650, 210/651, 653, 654, 500.42; 426/490, 492, 495, 662; 554/175

(56) References Cited

U.S. PATENT DOCUMENTS

| | | | |
|---|---|---|---|
| 4,062,882 A | 12/1977 | Sen Gupta | 260/428.5 |
| 4,093,540 A | 6/1978 | Sen Gupta | 210/23 |
| 5,516,924 A | 5/1996 | van de Sande et al. | 554/192 |
| 5,545,329 A | 8/1996 | LaMonica | 210/651 |
| 6,207,209 B1 * | 3/2001 | Jirjis et al. | 426/330.6 |
| 2003/0219716 A1 * | 11/2003 | Avdeef et al. | 435/4 |

FOREIGN PATENT DOCUMENTS

| | | | |
|---|---|---|---|
| CA | 1189087 | * | 6/1985 |
| DE | 3244007 A1 | | 6/1982 |
| DE | 284043 A5 | | 10/1990 |
| GB | 2084606 A | | 4/1982 |
| WO | WO 99/08459 | | 2/1999 |
| WO | WO 99/59707 | | 11/1999 |

* cited by examiner

*Primary Examiner*—Ernest G. Therkorn
(74) *Attorney, Agent, or Firm*—Baker Botts L.L.P.

(57) ABSTRACT

A process for refining and degumming edible oils by ultrafiltration which produces a permeate fraction with reduced phosphatide content and retentate with increased phosphatide content, and wherein the ultrafiltration membrane is composed of a polymerical polymer of a vinylidene difluoride monomer.

17 Claims, No Drawings

DEGUMMING OF EDIBLE OILS BY ULTRAFILTRATION

RELATED APPLICATIONS

This application claims priority under 35 U.S.C. §119 of PCT application number PCT/US01/16747, filed May 24, 2001, entitled "Degumming of Edible Oils by Ultrafiltration" which claims priority to U.S. provisional application No. 60/206,885 filed May 24, 2000.

BACKGROUND OF THE INVENTION

1. Field of the Invention

The invention relates to a process for refining and degumming edible, industrial and specialty oils by ultrafiltration, leading to a permeate fraction with reduced phosphatide content and a retentate with increased phosphatide content, wherein the ultrafiltration membrane is composed of a polymer or copolymer of a vinylidene difluoride monomer.

2. Background of the Related Technology

Crude vegetable, nuts and animal oils and fats are produced by a large variety of processes (J. M. Fils, *The production of oils in Edible Oil Processing*, eds. W. Hamm and R. J. Hamilton, Sheffield Academic Press, Sheffield, 2000) and extraction with an organic solvent such as hexane, is one of these processes. This extraction process utilizes an organic solvent, such as hexane, and produces a solution of crude oil and the organic solvent, which is commonly referred to as "miscella."

Another process involves pressing the oil-bearing material in, for example, a mechanical screw press. This leads to crude pressed oil and a press cake which still contains appreciable amounts of residual oil. It is common practice to recover this residual oil by extracting the press cake with solvent.

In known processes, crude oils typically are degummed, refined, bleached and deodorized to remove undesirable compounds including: free fatty acids (FFAs), phosphatides, particulate matter like meal residues, coloring materials like chlorophylls and xanthophylol, and miscellaneous non-saponifiable materials. For example, in processing soybean oils, the first step is degumming to remove the phosphatides for the production of lecithin. Water degumming is a conventional degumming method. When water is added to crude oil, most of the phosphatides in the oil are hydrated and become insoluble in oil. The hydrated gums are then separated from the oil by centrifugation. Next, the FFAs are reacted with sodium hydroxide to produce soaps, which are then removed along with residual phosphatides by centrifugation. Some pigments and destabilizing peroxides are then adsorbed by, for example, acid-activated bleaching clay; and finally, the oil is heated under high vacuum with steam sparging to strip trace amounts of FFAs, aldehydes and ketones, and other volatile compounds.

Considerable amounts of energy in the form of steam or electricity are required in these processes, and each step of the process of making edible oil only removes one or two types of undesirable components. If crude oil is not properly processed, treatment during the following steps will be more difficult and time and labor consuming. In addition to the energy costs, caustic refining, water washing and bleaching steps produce various streams such as high biological oxygen demand (BOD) acidic waste water and spent bleaching clay that either need to be treated or recovered due to economical or environmental reasons.

In conventional refining processes, free fatty acids, undesirable flavors, odor and color compounds, and other natural components like the phosphatides, must be removed from crude vegetable oils before they are used for food. Unfortunately, a "refining loss" 3–4 times greater than the free fatty acids content is often experienced, and considerable quantities of salable "neutral oil" is lost.

Processes for refining glyceride oils utilizing semi-permeable membranes have been disclosed in literature. U.S. Pat. Nos. 4,062,882 and 4,093,540 to A. K. Sen Gupta describe a process for refining a crude glyceride oil composition by passing a solution of this oil in an organic solvent under pressure over a semi-permeable membrane. In this process, the membrane retains the phosphatides present in the oil solution as a result of which the oil solution passing through the membrane shows a reduced phosphatide content. The membranes described in U.S. Pat. No. 4,093,540 are made of polyacrylnitrile. The membranes described in U.S. Pat. No. 4,062,882 are made of polyacrylonitrile, a polysulphone and a polyamide.

In U.S. Pat. No. 4,553,501 to Sen Gupta, a membrane filtration process is described that not only removes the phosphatides present in the crude triglyceride oil but also the free fatty acids present therein by the addition of a base to the miscella. In addition to the polyacrylonitrile, polysulphone, and polyamide membranes mentioned above, polyimide anisotropic membranes are also used for this purpose. Membranes made of these polymers are also described in PCT 00/42138 to Jirjis et al.

Polyimide membranes are also described in U.S. Pat. No. 4,414,157 to Iwama et al. U.S. Pat. No. 4,545,940 to Mutoh et al. describes a membrane used for the dewaxing of triglyceride oils that consists of a copolymer of ethylene and tetrafluoroethylene. In addition to waxes, phospholipids and free fatty acids were also retained by this membrane, but the disclosed flux is too low to be economic.

A subsequent paper (S. S. Köseoğlu, J. T. Lawhon and E. W. Lusas, *Journal American Oil Chemists' Society*, 67 (5), 315–322, 1990) on the suitability of a number of ultrafiltration membranes, reported that membranes made of polyamide were the least affected by hexane, but that a membrane made from a fluorinated polymer was deteriorated by hexane.

SUMMARY OF THE INVENTION

Accordingly, a need has arisen for refining and degumming oils in a process which has improved separation and which is more economical and more environmentally suitable than known methods.

In accordance with the present invention, a process for refining and degumming oils by ultrafiltration is provided that significantly improves the quality of the edible oils and lecithin products and is more economical and environmentally suitable than known methods. The inventive process contacts oil with an ultrafiltration membrane, wherein the ultrafiltration membrane comprises a polymer or copolymer of a vinylidene difluoride monomer, and separates the oil into a permeate fraction having a reduced phosphatide, color and free fatty acids content and a retentate fraction having an increased phosphatide content.

Accordingly, an object of the present invention is to provide ultrafiltration membranes that can be profitably used in the refining and degumming of solutions of oils in organic solvents by an ultrafiltration process.

It is a further object of the invention to provide membranes for the refining and degumming by ultrafiltration of pressed oils, conducted in the absence of solvent.

A further object of the invention is to provide edible oil products and lecithin products prepared by ultrafiltration which have significantly improved qualities over known edible oil products and lecithin products.

The ultrafiltration membranes according to the present invention (i.e., comprised of a polymer or copolymer of a vinylidene difluoride monomer): (1) are hexane-resistant, i.e., they retain their strength and do not swell in hexane so that they retain their permeability and selectivity, (2) withstand the pressure drop over the membrane during ultrafiltration; (3) have a good permeability for triglyceride oil and its solvents, which results in a relatively high flux through the membrane during the ultrafiltration process; (4) retain free fatty acids, coloring pigments and phosphatides from pressed oil and/or miscella and thus show a high selectivity, (5) do not unduly suffer from fouling, i.e., rinsing the membrane with solvent, permeate or miscella at regular (but not too frequent) intervals restores the membrane flux to a fully acceptable and constant level.

DETAILED DESCRIPTION OF SPECIFIC EMBODIMENTS

In the process of the present invention, "crude oil" (substantially unrefined, unprocessed oil) is contacted with an ultrafiltration membrane. If the crude oil is combined with a solvent, either as a result of extracting the crude oil from vegetable products or from the addition of solvent to improve separation, it is referred to as "miscella." If crude oil is recovered from vegetable products using physical methods, such as pressing, expellers, expanders, and/or extruders, and the oil is substantially free of solvent, it is referred to herein as "pressed oil."

The oil (from, for example, pressed oil) or oil and solvent which pass through the pores of the ultrafiltration membrane are referred to as "permeate." The phosphatides and oil which do not pass through the ultrafiltration membrane are referred to as "retentate." The retentate stream is preferably further treated to produce a lecithin product.

In the preferred processes, solvent is added to the retentate fraction, and this is contacted with an ultrafiltration membrane, which separates this retentate fraction with added solvent into a secondary permeate stream and a secondary retentate stream. By controlling the ultrafiltration membrane area and by selectively contacting the retentate fraction with added solvent with additional ultrafiltration membranes, the amount of oil in the secondary retentate stream (consisting primarily of phosphatides) can be selectively controlled to yield, upon evaporation, a lecithin product having an oil content of about 3 wt % to about 40 wt % or a substantially oil-free lecithin powder product. In the edible oil industry, it is common practice to define the lecithin product by its percentage of acetone insoluble compounds (consisting primarily of phosphatides), and thus, a lecithin product having an oil content of about 3 wt % to about 40 wt % would have an acetone insoluble content of about 60 wt % to about 97 wt %.

The permeate streams are preferable further refined, processed or treated to produce a high quality edible oil product, referred to herein as "an edible oil product" or "refined oil."

An improved process for processing crude oil is provided by the present invention by employing a membrane composed of a polymer or copolymer comprising vinylidene difluoride monomers that is incorporated in an ultrafiltration module. Such a module may contain a number of tubular membranes mounted inside a shell in such a way that the miscella fed to the module is divided over the different tubes. The permeate then emerges in the space between the tubes inside the shell so that it can be collected. The flows through each tube are collected at the other end of the module and constitute the retentate. Other ultrafiltration modules, such as, for example, spiral wound modules also exist and fall within the scope of the present invention.

Good results in degumming miscella have been obtained by using a polyvinylidene difluoride (PVdF)-membrane according to the present invention with a molecular weight cut-off (MWCO) of 30,000 dalton to 200,000 dalton. Lower MWCO's, as for example 9,000 dalton, can also be used, but they are only slightly more selective and their flux is lower. The preferred MWCO is about 5,000 to about 500,000 daltons. The most preferred MWCO is about 10,000 to about 250,000 dalton.

Using a membrane with a higher MWCO leads to a higher flux and thus to savings in the investments required for a given degumming capacity but can lead to a decrease in selectivity. However, it has been found that this decrease can be effectively counteracted by forming a small amount of soap in a pressed oil or miscella being processed by partially neutralising the free fatty acids present therein. Consequently, the membranes according to the invention can also profitably be used for degumming crude pressed oils.

When a miscella comprising solvent, triglyceride oil and phosphatides is fed to such an ultrafiltration module, its membrane will retain the phosphatides but allow the solvent and the triglyceride oil to pass through the membrane. Accordingly, the retentate will have a higher phosphatide content than the feed and the permeate will have a significantly lower phosphatide content than the feed. This means that the refined oil resulting from evaporating the solvent from this permeate and from bleaching the still residue can be physically refined to yield a high quality, fully refined edible oil.

If one considered a "filtration spectrum", the spectrum would include, on the low end for filtering low molecular weight components; nanofiltration, ultrafiltration, and microfiltration. Nanofiltration is generally suitable for filtering compounds having a molecular weight of about 200–8,000, ultrafiltration is generally suitable for filtering compounds having a molecular weight of about 4,000–500,000, and microfiltration is generally suitable for filtering compounds having a molecular weight of about 250,000–1,000,000. As used in this patent application, the term "ultrafiltration" is intended to include the entire range of nanofiltration, ultrafiltration, and microfiltration.

The ultrafiltration mode in the process according to the present invention is preferably a cross-flow filtration. This means that the miscella is pumped along the ultrafiltration membrane and that only a fraction of the solvent and oil present in the miscella permeates through the membrane per pass through the membrane tube. Accordingly, the retentate can be recycled to the feed of the module and/or it can be fed to a second and/or subsequent modules to attain a higher phosphatide concentration in the retentate (and thus a higher yield of degummed oil).

Especially in the production of "specialty oils" and/or "functional oils", for example, fish oil or borage oil, the conventionally known processes for refining and degumming the oil involve heating and/or the addition of chemicals which may alter the stability of the edible oil product. It is believed that the specialty oils and functional oils contain an increased level of double bonds which, upon heating or chemical addition (as in conventionally known processes), may decompose or form polymers, altering the stability of the edible oil product. It is believed that other crude oils also contain double bonds (though at a significantly reduced level) and these double bonds are similarly altered during heating or upon the addition of chemicals in the conventionally known processes. A key feature of the present invention is the production of an edible oil product accomplished without heating and addition of chemicals as is done in the conventionally known processes, and thus, the present invention maintains the oil in its naturally occurring stable chemical composition and structure.

The oil produced from the permeate fraction may be slightly off-color, and bleaching the oil with an adsorbent such as clay, activated clay, activated carbon and bone black, may be required to produce an acceptable color oil.

The oil produced from the permeate fraction may be slightly off-odor, and a deodorizing step may be required to produce an oil having an acceptable odor.

In order to obtain a substantially oil-free retentate, it is preferred to dilute concentrated retentate with fresh solvent. This fresh solvent reduces the retentate viscosity and also compensates for the preferential permeation if any, of the solvent through the membrane. If there is a preferential solvent flow through the membrane, the Oil Concentration Factor (OCF) will be markedly lower than the Volumetric Concentration Factor (VCF). Then the oil concentration in the feed will be higher than its concentration in the permeate and, for mass balance reasons, the oil concentration in the retentate will be even higher, adding fresh solvent to the retentate will redress this situation.

Diluting the retentate with fresh solvent and its subsequent concentration by ultrafiltration will thus allow a substantially oil-free solution of phosphatides to be obtained. A substantially oil-free lecithin powder product can be produced from this solution by evaporating the solvent, for instance in a spray tower. Conventional oil-free lecithin powder is normally produced by de-oiling conventional standard lecithin, using either acetone or a liquefied hydrocarbon, such as propane. In conventional processes, this de-oiling constitutes a separate process step, and thus makes de-oiled lecithin an expensive product. Producing a substantially oil-free lecithin powder product according to the present invention is thus more economical than the conventional process.

Lecithin products can be produced by the process according to the present invention by controlling the oil content in a secondary retentate stream, i.e., the retentate stream produced upon contacting the retentate fraction with added solvent with an ultrafiltration membrane. In a preferred embodiment, the secondary retentate stream, having a concentrated phosphatide content, is processed to either a substantially oil-free lecithin powder product or a lecithin product (having an acetone insoluble content of about 60 wt % to about 97 wt %) without hydration (addition of water) so as to keep the phosphatides in their naturally occurring chemical composition and structure.

In the production of lecithin products by conventional processes, the phosphatides are hydrated (treated with water), and miscibility and density is used to separate the hydrated phosphatide and the oil in a centrifuge separation. Then, the hydrated phosphatide is dried to form a lecithin product. It is believed that the conventional lecithin product has a significant shortcoming in that the hydration process and subsequent drying alters the chemical composition and/or structure of the naturally occurring phosphatides. A key feature of the present invention is the production of a substantially oil-free lecithin powder product and/or a lecithin product (having an acetone insoluble content of about 60 wt % to about 97 wt %) accomplished without a hydration step and subsequent drying step, and thus, maintaining the phosphatides in their naturally occurring chemical composition and structure.

In a somewhat less preferred embodiment, the solvent is removed from the secondary retentate stream by evaporation and the evaporation residue is treated with conventionally known processes such as water degumming, acid degumming and acid refining, such that a gum phase is formed that can be separated from the oil phase by centrifuge and then dried conventionally, for instance in a wiped film evaporator. This less preferred embodiment of the invention produces a conventional, standard quality lecithin which can be sold into existing markets. The oil phase resulting from the centrifugal separation can be recycled into the process, i.e., added to the oil prior to the oil contacting the ultrafiltration membrane, or, if a purge is found to be needed, processed by conventional alkali refining, acid degumming or acid refining processes.

The process according to the invention can also be used for pressed oils, i.e., oils that do not contain solvent. Therefore, the process according to the present invention is particularly suited for plants that produce both pressed oil and extraction oil since the latter arises in miscella form. Then, the pressed oil is subjected to the ultrafiltration process until the retentate has become too viscous and the permeate flux has become unacceptably low, after which the retentate may be mixed with the miscella resulting from the extraction process. The permeate obtained during the press oil filtration can be physically refined after having been bleached to yield a fully refined, high quality oil. Similarly, the permeate obtained during the miscella ultrafiltration can be physically refined after its solvent has been evaporated.

In using membranes to separate the phosphatides from oil, the oil (triglycerides) and phosphatides may have similar molecular weights, making them difficult to separate with membranes. Phosphatides have both hydrophilic and hydrophobic ends, and thus, in non-aqueous environments (i.e., upon addition of a solvent) they form reverse micelles with globular structures. The micelles formed have a significantly increased molecular weight, thus improving membrane separation. A key feature of the present invention is that it allows ultrafiltration of pressed oil without the addition of solvent, such that the conventionally known phosphatide micelles are not formed.

The membranes used when degumming pressed oils according to the process of the present invention preferably have a rather high MWCO so that the membranes exhibit an increased flux. This increased flux is desirable since it allows more viscous products such as triglyceride oils to be profitably processed. On the other hand, the high MWCO may decrease the selectivity of the ultrafiltration process and cause some phosphatides to permeate through the membrane. According to one embodiment of the present invention, this decrease in selectivity can be effectively counteracted by adding a small amount of soap to the pressed oil being subjected to the ultrafiltration treatment. According to the invention, the soap can also be formed in situ by the addition of a base, such as a small amount of an hydroxide, such as caustic soda, or similar base, such as for instance a soluble silicate, such as sodium metasilicate. The amount of base should preferably be less than the equivalent amount of free fatty acids present.

The exact role of the soap is not clear, but it is possible that the soap serves to incorporate the phosphatide into a globular structure, somewhat similar to the micelles formed when solvent is added to crude oil, and effectively increases the size of the phosphatides, such that the phosphatides are retained by the membrane. Soaps are not found in the permeate, so that this can be physically refined without subjecting it to a soap removal treatment. The soaps in the retentate may require a soap removal treatment because of excessive foaming during subsequent retentate treatment.

It has also been found that the addition of surfactants serves to significantly improve the ultrafiltration of pressed oils. It has further been found that polar solvents, such as alcohols, for example, methanol, ethanol, and isopropyl alcohol, and water, significantly improve the ultrafiltration of pressed oils. While the exact role of surfactants and polar solvents is not known, it is believed that the addition of surfactants and/or the addition of polar solvents serve to incorporate the phosphatides into a globular structure, somewhat similar to micelles, which increases the effective molecular weight of the phosphatides, such that the ultrafiltration membrane provides suitable separation of the phosphatides and oil from pressed oils without the addition of solvents such as hexane.

It is not uncommon that membranes as delivered by their manufacturers are kept moist by water or aqueous glycerol. Then, the membrane is preferably conditioned beforehand by exposing it to solvents of decreasing polarity in a way that is known to those skilled in the art. Suitable solvents are, for example, an alcohol, such as isopropanol, to dissolve and remove the water and glycerol, and then hexane to remove the isopropanol. In this context, an intermediate rinsing with a mixture of isopropanol and hexane has been found to be quite effective.

It is preferable to subject the miscella or the pressed oil to a pre-filtration process before contacting with the ultrafiltration membrane. This pre-filtration process should remove meal fines and other particulate matter and thereby protect the ultrafiltration membrane against fouling. For this pre-filtration process, conventionally known units used to treat crude oil or miscella destined for the isolation of brilliant lecithin have been found to be fully adequate. The resulting filter cake can easily be disposed of via the meal and, if it contains solvent, by feeding it to a meal desolventising unit.

The crude oil may be at least partially degummed by conventional processes prior to contacting the oil with an ultrafiltration membrane. This increases the flux rate and allows fewer membrane modules to be used. Also, this lessens the frequency at which the membranes must be rinsed.

For capacity reasons, several ultrafiltration modules may be required in an industrial environment. These can be in parallel or in sequence, and a set of parallel modules can also be in sequence with a subsequent set of parallel modules. The size and number of modules in each set and the flow configuration is dependent upon the degrees of concentration achieved, the permeate fluxes attained through the membrane, and module cost. The most cost effective installation is preferably designed by mathematical modelling.

The temperature of the pressed oil or miscella during the ultrafiltration according to the present invention has been found not to be critical. If a miscella is processed, its temperature is preferably below the boiling point of the solvent for safety reasons, but higher temperatures also fall within the scope of the present invention. If a pressed oil is subjected to ultrafiltration according to the invention, its temperature may be raised since this reduces the viscosity of the oil, and thus its flux through the membrane. On the other hand, an increase in temperature may also affect the permeability and selectivity of the membrane. Accordingly, membrane properties should be determined experimentally and the results can then be used in arriving at an optimal situation.

Experiments should also be conducted to investigate the effect of pressure and linear flow rate on the flux through the membrane. In general, a higher pressure will lead to a higher flux, but it may also accelerate membrane fouling, and thus necessitate more frequent cleaning. In addition, a higher pressure may make cleaning the membrane more difficult in that it takes longer to re-establish the acceptable level of flux.

When a tubular membrane is used in the process according to the invention, cleaning by back flush is generally not possible. In that instance, rinsing the membrane with solvent by switching from retentate to solvent has been found to be the most effective way of cleaning the membrane. Switching to miscella is also acceptable, but is generally less effective than using fresh solvent. The use of permeate as rinsing medium has been found to be quite effective and may in practice be the most cost effective medium.

EXAMPLE 1

Crude corn oil containing 1.83% free fatty acids expressed as oleic acid and with a phosphatide content corresponding to 796 ppm phosphorus was diluted with hexane to form a miscella of 25% (wt/wt) oil content. This miscella was fed to an ultrafiltration unit of 1.2 m length and containing 5 tubular membranes with an internal diameter of 6 mm so that the total membrane surface was 0.11 $m^2$. The membrane was made of polyvinylidene difluoride (XP-183 produced by PCI Membranes, Whitchurch, UK) and had a MWCO of 30,000 dalton. The flow rate was 1,200 l/h while a trans-membrane pressure of 3.5 bar was maintained. The miscella temperature was 55° C., i.e., thus just below the boiling point of hexane.

Before the experiment proper started, the membrane as supplied by the manufacturer was conditioned by rinsing it with isopropanol to remove the water and glycerol. Subsequently, it was rinsed with a mixture of isopropanol and hexane, and finally, with hexane to remove the isopropanol. In the very early stages of the experiment, the membrane thus conditioned showed a poor phosphatide retention but very rapidly, a low and stable residual phosphorus content of the permeate established itself.

The phosphorus content of the combined permeate was only 10.5 ppm P expressed on oil, indicating a phosphatide retention of almost 99%. When the same corn oil was water degummed, a residual phosphorus content of 40 ppm was observed, which observation indicates that the membrane also retained some non-hydratable phosphatides. Accordingly, the phosphorus content of the retentate of this experiment had increased considerably to 3,261 ppm P expressed on the oil in the retentate.

The initial flux in this experiment was 100 $l/m^2h$ but it dropped during the course of the experiment. It could however be restored to near initial values by rinsing the membrane with hexane; this was done at volume concentration factors (VCF) 2 and 4 so that an average flux of 77 $l/m^2h$ resulted. The final flux at a VCF of 8 was 55 $l/m^2h$.

The experiment also showed that the membrane had a higher permeability for hexane than for triglyceride oil since the VCF of 8 corresponded to an oil concentration factor (OCF) of 4. Consequently, the phosphorus content of the retentate also increased by a factor of approximately 4 from 796 ppm to 3,261 ppm expressed on oil.

The example clearly shows that the use of the membrane according to the present invention leads to excellent phosphatide retention while exhibiting a high flux through the membrane. It also shows that this high flux could be maintained by rinsing the membrane.

EXAMPLE 2

Crude soybean oil containing 1799 ppm P and a free fatty acid content of 0.61 wt % expressed as oleic acid was treated as described in Example 1 and a permeate resulted that had a phosphorus content of 6.3 ppm P on oil. The solvent was evaporated and the resulting still residue was treated with 0.20 wt % citric acid treated rice hull ash under vacuum at 99° C. for a period of 15 min after which the adsorbent was removed by filtration. Subsequently, the oil was bleached at 105° C. and under vacuum while using 0.95 wt % bleaching earth (Filtrol 105 WF) for a period of 15 min; again, the adsorbent was removed by filtration. The filtrate was subjected to a physical refining process at 257° C. for a period of 1 hour 15 min. Samples were taken and analysed. The analytical data are given in Table 1.

TABLE 1

| Property/sample | permeate | after treatment with rice hull ash | after treatment with bleaching earth | after physical refining |
|---|---|---|---|---|
| free fatty acids (wt %) | | 0.17 | 0.16 | 0.02 |
| Lovibond colour Y/R | | 30/10 | 40/5.4 | 1.0/0.1 |
| peroxide value | | 1.8 | 0.6 | 0 |
| anisidine value | | 1.2 | 1.4 | 1.0 |
| chlorophyll (ppm) | | 595 | 25 | 20 |
| phosphorus (ppm) | 0.63 | 0.06 | 0 | 0.1 |
| calcium (ppm) | 0.02 | 0.02 | 0.02 | 0.02 |
| magnesium (ppm) | 0.02 | 0.02 | 0.02 | 0.02 |
| iron (ppm) | 0.02 | 0 | 0 | 0.02 |
| copper (ppm) | 0 | 0 | 0.01 | 0 |
| nickel (ppm) | 0 | 0 | 0 | 0.02 |
| A.O.M. (h) | | | | 18 |

Table 1 clearly shows that excellent results are obtained by subjecting crude soybean oil to the process according to the present invention and then to standard bleaching and physical refining treatments. The taste of the fully refined oil was judged to be 9 on a scale of 1–10 and its keepability was fully acceptable.

EXAMPLE 3

In this experiment, a polyvinylidene difluoride membrane with a higher MWCO was used. The membrane material was FPT-20 (PCI Membranes) with a MWCO of 200,000. This corresponds to a pore size of approx. 0.1 micron so that the membrane could also be referred to as a microfiltration membrane instead of an ultrafiltration membrane The module contained 5 tubular membranes of 1.2 m length and 6 mm internal diameter so that the total surface area was 0.11 m$^2$. A 25% (wt/wt) miscella of crude soybean oil (free fatty acid content 0.58%; phosphorus content 765 ppm P) in hexane was subjected to ultrafiltration in this module at a temperature of 55° C., a trans-membrane pressure of 3.5 bar and a cross flow rate of 1 200 l/h; this corresponds to an average linear speed of 0.11 m/min.

Using a higher MWCO led indeed to a higher average flux of 114 l/m$^2$h up to a VCF of 7. At this concentration factor, the OCF was 4.2, thus showing a slightly higher permeability of this membrane for hexane than for triglyceride oil. Phosphatide retention was still excellent in that the phosphorus content of the permeate varied between 7 and 17 ppm P and that the phosphorus content of the retentate had increased to 3,090 ppm P at a VCF of 7.

EXAMPLE 4

Crude cottonseed pressed oil was subjected to an ultrafiltration process using the XP-183 membrane of Example 1. However, before treating the oil, a stoichiometric amount of sodium metasilicate was added to the pressed oil. This addition caused the free fatty acid content of the permeate to be reduced from 1.8% to 0.2%. At the same time, the phosphorus content of the feed, 884 ppm P, decrease to only 12 ppm in the permeate. Gossypol content of the oil was reduced from 0.42 wt % to 0.22 wt %. This example shows that the presence of soaps does not interfere with the selective rejection of phosphatides. It also shows that soaps do not permeate through the membrane.

EXAMPLE 5

The retentate resulting from Example 1 containing 3,261 ppm P was subjected to a water degumming treatment. If only little water was used, hardly any gums were formed and the "degummed" oil still showed an appreciable residual phosphorus content. However, when the retentate was degummed with 10 wt % water, the resulting oil showed a phosphorus content of only 170 ppm P. With a factor of about 30 for converting ppm phosphorus to ppm phosphatides, it can be concluded that this retentate contained about 10 wt % phosphatides. Apparently, the amount of water required for maximal degumming is about the same as the phosphatide content.

In Example 1, it was shown that this particular corn oil contained 40 ppm P after water degumming. Given the OCF of 4 attained in Example 1, it is highly probable that the residual phosphatides in the retentate have the same chemical composition as the non-hydratable phosphatides in the water degummed corn oil. Only their concentration is about 4 times as high since the oil was concentrated by a factor of 4. Retention of non-hydratable phosphatides by the ultrafiltration membrane was also indicated in another experiment in which a miscella of soybean oil containing 1,267 ppm P, 94 ppm Ca and 105 ppm Mg was subjected to ultrafiltration according to the invention. The permeate at a VCF of 2 contained only 3 ppm P, 0.14 ppm Ca and 0.17 ppm Mg. The chlorophyll content of the permeate was also decreased somewhat from 960 ppm in the starting oil to 430 ppm in the permeate.

The present inventive process of degumming oils is advantageous over known processes for processing edible oils. The present invention provides for commercially feasible ultrafiltration membrane separation of crude oils. Also, the present invention provides for the ultrafiltration of pressed oils without the addition (and subsequent removal) of solvents. Further, the present invention provides a process for producing lecithin products without undergoing a hydration step (and subsequent drying step) which alters the naturally occurring chemical composition and/or structure of the phosphatides. Still further, the present invention provides a process for producing edible oil products without undergoing the conventionally known heating or addition of chemical steps which alters the naturally occurring stable chemical composition and/or structure of the oils.

The invention, therefore, is well adapted to carry out the objects and attain the ends and advantages mentioned, as well as others inherent therein. While the invention has been depicted, described, and is defined by reference to exemplary embodiments of the invention, such references do not imply a limitation on the invention, and no such limitation is to be inferred. The invention is capable of considerable modification, alteration, and equivalence in form and function, as will occur to those ordinarily skilled in the pertinent arts and having the benefit of this disclosure. The depicted and described embodiments of the invention are exemplary only, and are not exhaustive of the scope of the invention. It is intended that all such variations within the scope of the invention, giving full cognizance to equivalence in all respects, be included within the scope of the appended claims.

What is claimed is:

1. A process for treating oil, comprising the steps of:
   (a) contacting the oil with an ultrafiltration membrane, wherein the ultrafiltration membrane comprises a polymer or copolymer of a vinylidene difluoride monomer;
   (b) separating the oil into a permeate fraction having a reduced phosphatide content and a retentate fraction having an increased phosphatide content; and
   (c) treating the retentate fraction to produce a lecithin product.

2. The process claim 1, wherein the step of contacting the oil with the ultrafiltration membrane is conducted in the absence of solvent.

3. The process claim 1, wherein treating the retentate fraction further comprises the steps of:
   (a) adding a solvent to the retentate fraction;
   (b) contacting the retentate fraction with added solvent with an ultrafiltration membrane, wherein the ultrafiltration membrane comprises a polymer or copolymer of a vinylidene difluoride monomer;
   (c) separating the retentate fraction with added solvent into a secondary permeate stream and a substantially oil-free secondary retentate stream; and
   (d) evaporating solvent from the secondary retentate stream to produce a substantially oil-free lecithin powder product.

4. The process claim 1, wherein treating the retentate fraction further comprises the steps of:
   (a) adding a solvent to the retentate fraction;
   (b) contacting the retentate fraction with added solvent with an ultrafiltration membrane, wherein the ultrafiltration membrane comprises a polymer or copolymer of a vinylidene difluoride monomer;
   (c) separating the retentate fraction with added solvent into a secondary permeate stream and a secondary retentate stream; and
   (d) evaporating solvent from the secondary retentate stream to produce a lecithin product having an acetone insoluble content of about 60 wt% to about 97 wt%.

5. The process claim 1, further comprising the step of adding soap to the oil prior to contacting the oil with the ultrafiltration membrane.

6. The process of claim 1, further comprising the step of adding a surfactant to the oil prior to contacting the oil with the ultrafiltration membrane.

7. The process of claim 1, further comprising the step of adding a polar solvent to the oil prior to contacting the oil with the ultrafiltration membrane.

8. The process of claim 7, wherein the polar solvent is selected from the group consisting of alcohol, water, and a combination of alcohol and water.

9. The process of claim 1, further comprising the step of prior to contacting the oil with an ultrafiltration membrane, forming soaps in situ by the neutralization of free fatty acids present in the oil by the addition of a base.

10. The process of claim 9, wherein the neutralization is limited to a partial neutralization.

11. The process of claim 9, wherein the base is selected from the group consisting of an hydroxide, a soluble silicate, and a combination of an hydroxide and a soluble silicate.

12. The process of claim 1, wherein the ultrafiltration membrane has a molecular weight cut-off in the range of about 5,000 daltons to about 500,000 daltons.

13. The process of claim 1, wherein the ultrafiltration membrane has a molecular weight cut-off in the range of about 10,000 daltons to about 250,000 daltons.

14. The process claim 1, further comprising the step of pre-filtering the oil prior to contacting the oil with the ultrafiltration membrane.

15. The process of claim 1, further comprising the step of at least partially degumming the oil prior to contacting the oil with the ultrafiltration membrane.

16. The process of claim 1, wherein the step of treating the retentate fraction comprises a treating process selected from the group consisting of water degumming, acid degumming, and acid refining.

17. The process of claim 1, wherein the steps are performed in a continuous process and the step of treating the retentate fraction yields a degummed retentate stream which is added to the oil prior to contact with the ultrafiltration membrane.

* * * * *